United States Patent [19]
Rose et al.

[11] Patent Number: 5,147,357
[45] Date of Patent: Sep. 15, 1992

[54] MEDICAL INSTRUMENT

[76] Inventors: Anthony T. Rose; Theresa M. Rose, both of 741 Lakefield Rd., Suite G, Westlake, Calif. 91361

[21] Appl. No.: 670,955

[22] Filed: Mar. 18, 1991

[51] Int. Cl.$^5$ .............................................. A61B 17/39
[52] U.S. Cl. ..................................... 606/49; 606/51; 606/52
[58] Field of Search ................... 606/1, 36, 37, 39–52, 606/167, 170, 171, 205–209; 29/268; 128/751, 754

[56] References Cited

U.S. PATENT DOCUMENTS

| | | | |
|---|---|---|---|
| 2,068,721 | 1/1937 | Wappler et al. | 606/51 |
| 4,512,343 | 4/1985 | Falk et al. | 606/52 |
| 4,887,612 | 12/1989 | Esser et al. | 128/751 |
| 4,957,498 | 9/1990 | Caspari et al. | 606/146 |

Primary Examiner—Peter A. Aschenbrenner
Attorney, Agent, or Firm—Roger A. Marrs

[57] ABSTRACT

A medical instrument as a forcep is disclosed herein having pivotal handles carried on an instrument body from which an elongated tube projects enclosing a push-pull rod. The rod carries a pivotal jaw arrangement and outwardly projecting from the tube for grasping or gripping purposes. The other end of the rod is coupled to the handle for actuation of the jaw arrangement by either push rod or pull rod functioning. A spherical piston gear interconnects the rod end with the jaw arrangement and a rod travel limit stop is operably connected between the handle, rod and instrument body. An electrode is carried on the body in installed fashion for supplying energy to the rod and jaw arrangement for cauterizing purposes.

7 Claims, 3 Drawing Sheets

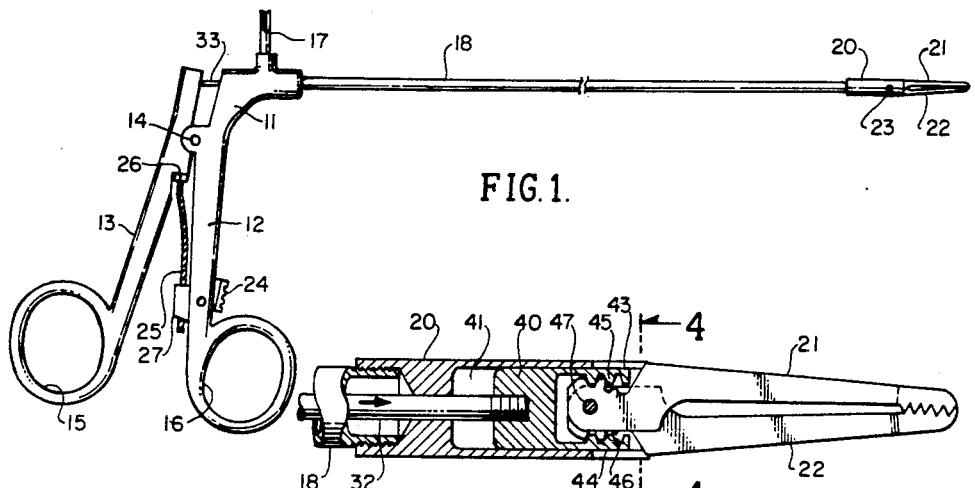
FIG. 1.
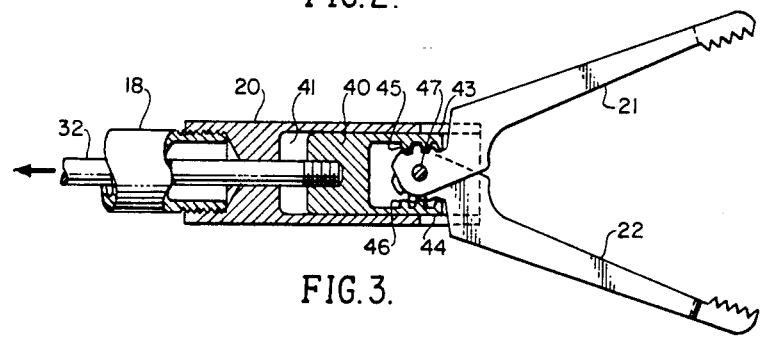
FIG. 2.
FIG. 3.
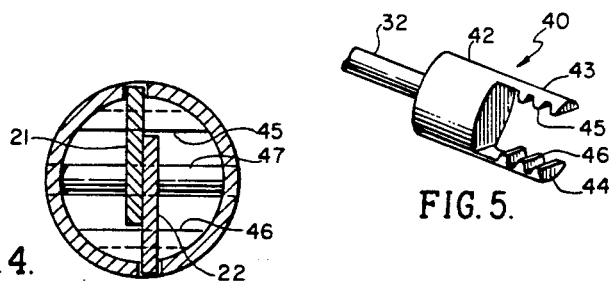
FIG. 4.
FIG. 5.
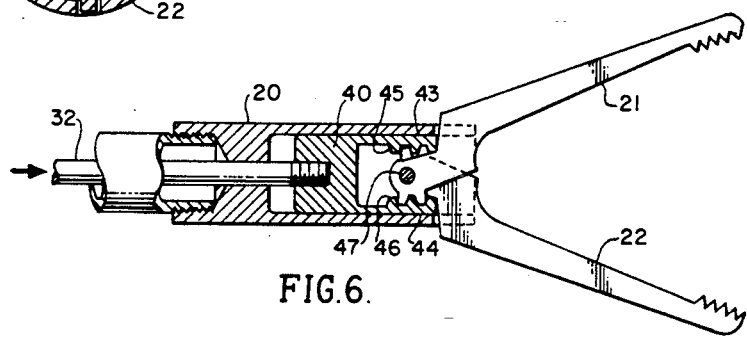
FIG. 6.

MEDICAL INSTRUMENT

BACKGROUND OF THE INVENTION

1. Field of the Invention

The present invention relates to the field of medical instruments, and more particularly to a novel surgical instrument having a hand-operated draw arrangement adapted to grasp or grip a variety of articles or substances. In one application, the surgical instrument is employed to facilitate the removing of animal or human tissue. In this sense, tissue is to comprise skin, cartilage or any other cellular animal growth.

2. Brief Description of the Prior Art

It is the conventional practice for medical practitioners, surgeons or the like to utilize instruments to remove tissue from animal or human beings. The instrument is utilized to remove tissue from an inaccessible region of the body as through a natural body opening or through a surgically provided opening within the human or animal body. Such a common type of an instrument utilizes a pair of jaws with one of the jaws being movable with respect to the other jaw. The movable jaw is to be movable within a cavity of the fixed jaw. Around the fixed jaw a cutting edge is sometimes provided and during movement of the movable jaw within the fixed jaw, the tissue located therebetween is severed and this becomes located within the cavity. The medical instrument is then removed from the body and the severed tissue removed with the instrument.

Problems and difficulties have been encountered when employing such conventional instruments because of the space required for use of the instrument. It is desirable to have the instrument as small in size and physical area as possible and as small in cross-section as possible. At the present time, a typical dimension in cross-section would be no more than $\frac{1}{2}$ to 1 centimeter. When dealing with such small dimensions, the instrument is fragile and even though constructed of metal, will sometimes bend, break or easily fatigue so that it is subsequently damaged. Frequently, the instrument breaks and this is extremely undesirable since such instruments are relatively expensive pieces of equipment. There is also the possibility that a broken portion of the instrument could be separate from the main portion of the instrument and become lodged in the body cavity. This requires utilization of other instruments to remove the broken piece or possibly expanding the surgical procedure in order to remove broken instrument pieces.

Furthermore, the precise opening and closing of the jaw arrangement is critical and control of push or pull rods for expanding the jaws is necessary so that the surgeon has the required control of the instrument. Furthermore, it is extremely helpful to the surgeon to be able to cauterize the area in which the surgery is being performed and conventional instruments do not provide for achieving this procedure simultaneously with the withdrawal of tissue.

Therefore, a long-standing need has existed to provide a surgical instrument which is constructed of a small cross-sectional size that is of high strength and construction so as to minimize the possibility of breakage. Means for cauterizing the wound or surgical area is desirable as well as providing a limit stop for positioning or actuation of the jaw arrangement.

SUMMARY OF THE INVENTION

Accordingly, the above problems and difficulties are obviated by the present invention which provides a novel medical instrument for grasping or gripping portions of the human body which comprise an instrument body for supporting one end of an elongated tube through which a push-pull rod is reciprocally carried for movement therethrough. One end of the rod includes a geared arrangement for actuating a jaw arrangement upon the actuation of a handle lever pivotally mounted on the instrument body and connected to the end of the rod opposite to its end carrying the jaw arrangement. In one form of the invention, the gear arrangement includes a spherical piston gear having internal teeth in engagement with teeth arranged in a semicircle on the jaw arrangement. Means are interconnected between the instrument body and the handle lever for limiting the movement of the rod so that the user has control of the jaw arrangement and an electrode is carried on the instrument body and is insulated from the tube so that electrical energy may be safely provided to the rod and the jaw arrangements for effecting a cauterization procedure. A copper conducting pellet is introduced into a conductive chamber disposed between the end of the electrode and the insulated tubing for achieving maximum electrical conductivity during the procedure.

Therefore, it is among the primary objects of the present invention to provide a novel medical instrument which is of greatly reduced cross-sectional size and yet houses a minimum number of operating components necessary to actuate a jaw arrangement for grasping or gripping purposes.

Yet another object of the present invention is to provide a novel medical instrument having a special spherical piston gear operably connected to a jaw arrangement and operative in response to actuation of a push or pull rod so that the jaw arrangement will grasp or grip intended articles.

A further object of the present invention is to provide a novel surgical instrument of extremely small size in cross-section which will permit the surgeon to cauterize an operative area undergoing a procedural technique and yet permit grasping or gripping of tissues during the procedure.

Another object of the present invention is to provide a novel travel stop or limit means for controlling the opening and closing of a jaw arrangement by a push or a pull rod operated by a handle lever pivotally connected to the instrument body.

Yet a further object of the present invention is to provide a novel medical instrument having the ability to mount and operate a minimum number of parts with an extremely small volume area and of small cross-sectional dimension.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description taken in connection with the accompanying drawings in which:

FIG. 1 is a side elevational view of the novel medical instrument incorporating the present invention;

FIGS. 2 and 3 demonstrate another gear arrangement for operating the jaw arrangement that may be substituted for the arrangement shown in FIGS. 11 and 12 with respect to the instrument shown in FIG. 1;

FIG. 4 is a transverse cross-sectional view of the jaw arrangement shown in FIG. 2 as taken in the direction of arrows 4—4 thereof;

FIG. 5 is a front perspective view of the novel spherical piston gear used in the embodiment illustrated in FIGS. 2 and 3;

FIG. 6 is a view similar to the view of FIG. 3 illustrating the operation of the jaw mechanism by a push rod as opposed to the pull rod shown in FIG. 3;

DESCRIPTION OF THE PREFERRED EMBODIMENT

Figure 7:
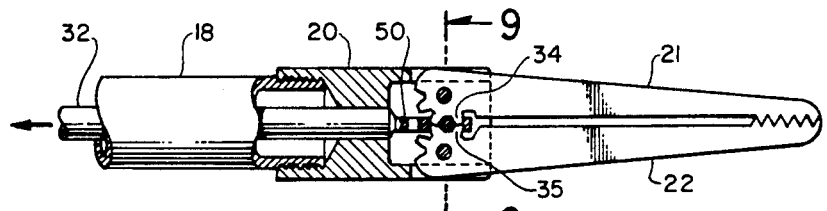
FIGS. 7 and 8 are enlarged views of another version of gear and jaw arrangement for use in the ; instrument shown in FIG. 1.

Referring to FIG. 1, an instrument body 11 is provided having a downwardly depending fixed member 12 serving as one portion of a handle, while the other portion is represented by a handle lever 13 pivotally mounted to the body by means of a pivot connection 14. The terminating ends of the respective handle portions 12 and 13 are provided with closed loops 15 and 16 through which the user's fingers may be inserted during the use of the instrument. The instrument further includes an electrode 17 carried on the instrument body 11 and insulated therefrom. Outwardly projecting from the body 11 and normal to the electrode 17 is an elongated tube 18 terminating in a fitting 20 which houses a jaw arrangement having pivoting jaws 21 and 22 operable about a pivot 23. Throughout this specification, it is to be undestood that the jaw arrangement may include a pair of jaws which pivot with respect to one another or may relate to a stationary jaw having the other jaw of the pair moving back and forth with respect to the stationary jaw. FIG. 1 also illustrates a stop means for holding the jaw arrangement in either an open, a closed, or a midway position, and such a limit stop means includes a finger-operated button 24 which engages with a cable 25 fixed at one end to the pivoting handle lever 13. Numeral 26 illustrates the securement of the cable end to the handle lever 13, while the opposite end of the cable is slidably mounted through a block 27.

Figure 11:
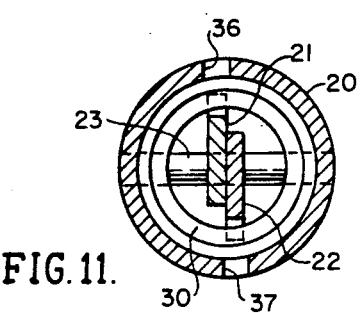
FIGS. 11 and 12 are enlarged cross-sectional views of the novel gearing and jaw arrangement employed in the embodiment shown in FIG. 1.
Figure 12:
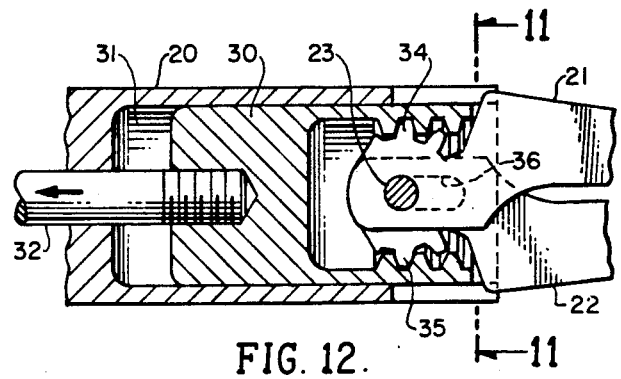

Referring now in detail to FIGS. 11 and 12, it can be seen that the tube fitting 20 houses a piston gear 30 that reciprocates within a compartment 31 as a rod 32 is moved back and forth. One end of the rod is attached to the end of the handle lever 13 by means of a connecting element 33, while the other end of the rod is threadably connected to the reciprocating piston gear 30. The respective jaws 21 and 22 of the jaw arrangement include teeth arranged in a semicircle, that are engaged with grooves provided in the open end of the piston gear 30. Teeth 34 are carried on jaw 21 while teeth 35 are carried on jaw 22. A slot 36 is provided in the side of the piston gear 30 through which the pivot pin 23 projects. The presence of the pin not only permits the jaws 21 and 22 to separate and be drawn together as the piston gear is moved within the chamber 31, but the pivot 23 prevents rotation of the piston gear or the jaws.

FIG. 11 shows that the respective jaws 21 and 22 pass through slots 36 and 37 provided in the tube fitting 20 as the jaw arrangement is operated by the actuating rod 32.

Referring now in detail to FIGS. 2 and 3, another version of gear and jaw arrangement is illustrated wherein the respective jaws 21 and 22 are operated by means of a spherical piston gear 40 operating within a chamber 41 defined in the fitting 20. The rod 32 is pulled in order to open the jaws, as illustrated in FIG. 3, and pushed forwardly in order to close the jaws, as shown in FIG. 2. The retainer 20 is threadably carried on the end of the tube 18, and the piston gear 40 is more clearly illustrated in FIG. 5.

In this latter FIGURE, it can be seen that the gear includes a cylindrical body 42 having outwardly projecting elements 43 and 44. Each of the elements includes teeth provided on their opposing surfaces, and the teeth are represented by numerals 45 and 46 respectively. These teeth are also illustrated in FIG. 4 and it can be seen that the space provided between the teeth accommodates placement of a pivot pin 47 about which the respective jaws 21 and 22 rotate as their semicircular teeth mesh with the teeth 45 and 46 in response to movement of the piston gear 40.

Referring to FIG. 6, the same arrangement is illustrated with the exception that the jaw arrangement opens upon the pushing of rod 32 so that the jaws 21 and 22 separate upon the pushing of the rod and close upon the pulling of the rod 32.

Figure 8:
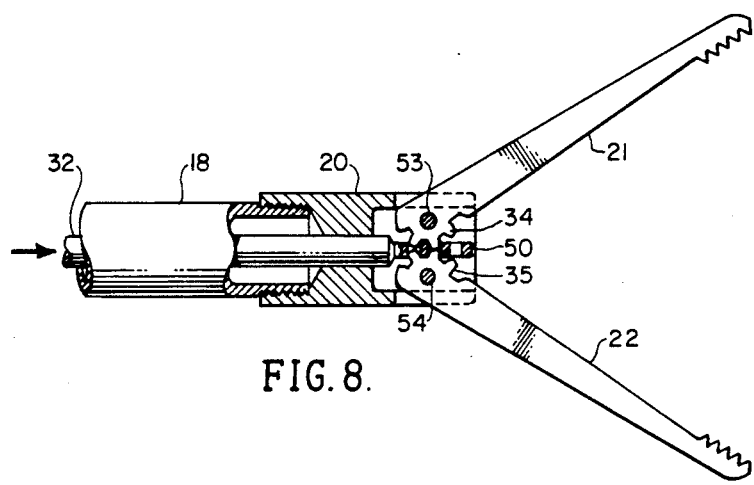
Figure 9:
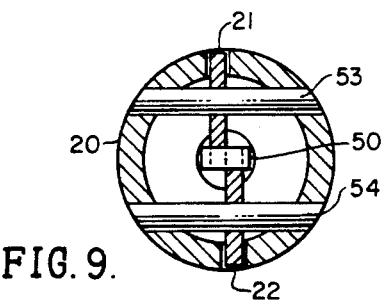
FIG. 9 is a transverse cross-section of the jaw arrangement shown in FIG. 7 as taken in the direction of arrows 9—9 thereof.
Figure 10:
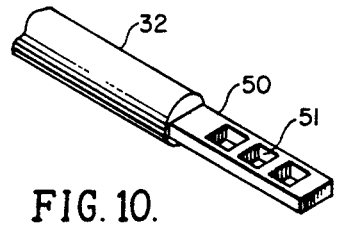
FIG. 10 is a front perspective view of a reciprocal actuator used in the version shown in FIGS. 7 and 8.

Referring now to FIGS. 7 and 8, another version of jaw arrangement is illustrated in which the jaws 21 and 22 are activated by means of a bar 50 carried on the extreme end of rod 32 and which moves in a reciprocal manner along the central longitudinal axis of the tube 18. The bar includes a plurality of openings and is more clearly illustrated in FIG. 10 wherein a central opening is indicated by numeral 51. The teeth 34 and 35 of the jaws 21 and 22 are aligned to mesh with the opening in the bar 50 as the rod 32 is pushed or pulled. As shown in FIG. 7, the rod is pulled rearwardly to close the jaws, while in FIG. 8, the rod is pushed to open the jaws. In FIG. 9, it can be seen that a pair of pivots 53 and 54 are employed about which the jaws 21 and 22 rotate respectively.

Figures 13, 14, 15:
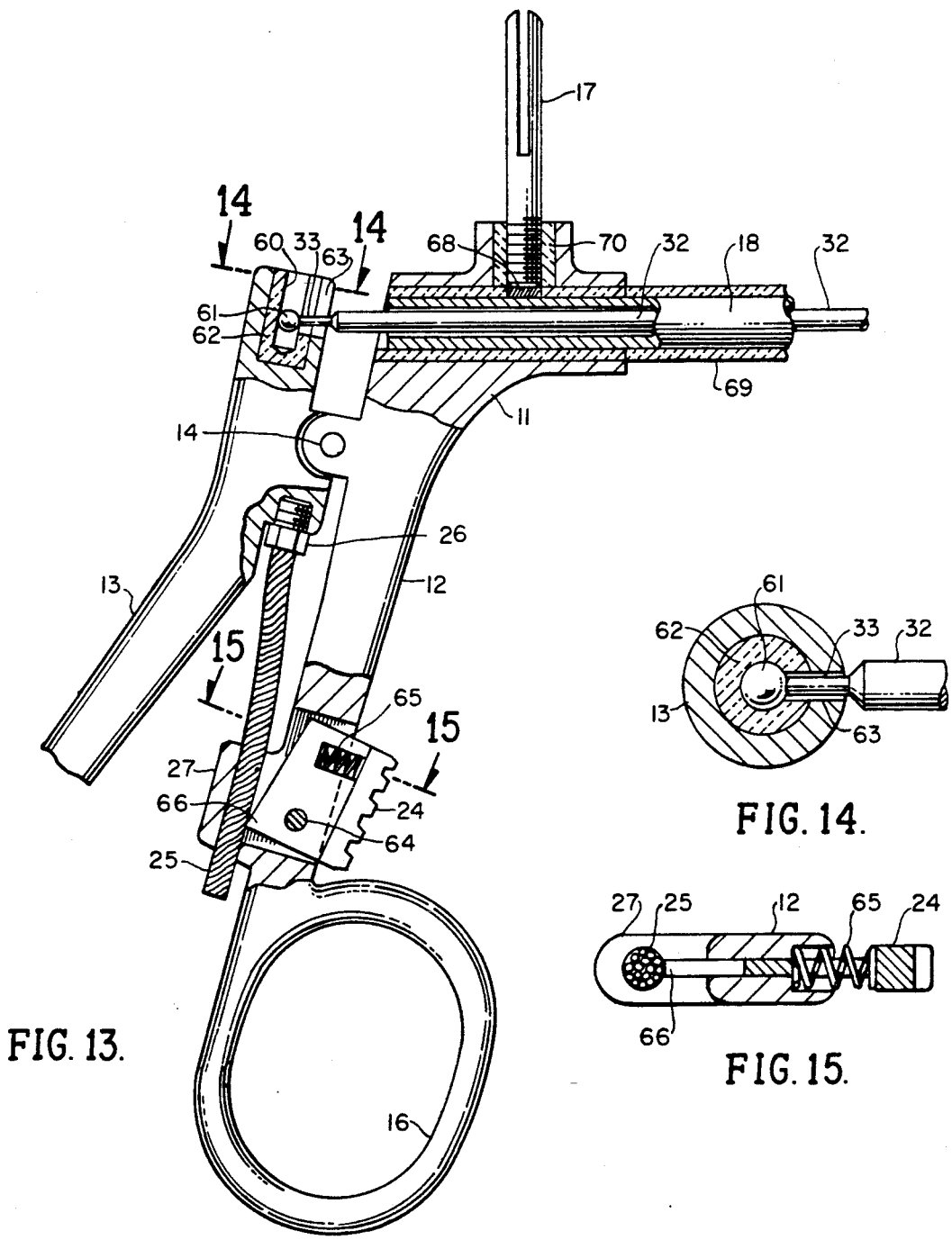
FIG. 13 is an enlarged view of the handle arrangement carried on the instrument body of the medical instrument shown in FIG. 1 and illustrating an actuating rod limit or stop means.
FIG. 14 is a sectional view of the connection between the handle lever and the rod end as taken in the direction of arrows 14—14 of FIG. 13.
FIG. 15 is a transverse cross-sectional view of the instrument body illustrating the stop mechanism latch.

Referring now in detail to FIGS. 13-15 inclusive, it can be seen that the handle lever 13 pivots with respect to the instrument body handle 12 via pivot 14. The upper end of the handle lever 13 includes a receptacle 60 into which a ball 61 is universally mounted. The ball is carried on the end of element 33 and is insulated from the material of the handle lever 13 by a thickness of insulation 62 as indicated in FIG. 14. The element 33 rides within an open-ended slot 63 as the arm pivots with respect to the stationary handle or instrument body 11.

It is also seen that the pushbutton 24 pivots about pivot 64 and includes a spring 65 normally biasing a stop corner 66 against the external surface of cable 25 to retain the cable and the handle lever 13 in the fixed position. While still fixed, the ride 32 will remain fixed and the jaws will be in the position so fixed. Once the pushbutton 24 has been pressed against the expansion of spring 55, the stop corner 66 will release the cable 25 and the handle lever 13 can be moved accordingly so as to advance or retract the rod 32.

It is also noted in FIG. 13 that the electrode 17 terminates in a chamber 68 that is occupied by a copper pellet. The end of the electrode 17 engages the pellet and the pellet serves as a super conductor through which electrical energy can be provided to the metal of the tubing 18. In order to insulate the tubing 18, an insulating cover 69 is employed which separates the handle portions of the instrument from the tubing 18. Therefore, the tubing 18 and the rod 32 can be electrically activated to provide resistance heating at the jaw arrangement when desired. Furthermore, insulation 70 separates the threaded engagement of the electrode 17 with the instrument body 11.

In view of the foregoing, it can be seen that the medical instrument of the present invention provides a novel jaw arrangement which is activated by a push rod or pull rod through a spherical gear or an apertured bar gear arrangement. The push rod or pull rod is operated by pivoting of the handle lever 13 to which one end of the rod is attached via the ball and slot arrangement 60, 61 and the opening or closing of the jaws as well as any mid position of the jaws is under control of the travel stop mechanism operated by the spring-biased pushbutton 24 and the cable 25.

The jaw arrangement is extremely reduced in dimension as well as volume or surface area, and the novel gearing operably connecting the end of the rod 32 with the jaw arrangement is responsible for permitting small size and reduced dimension as well as reduced cross-section of the components.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A medical instrument of the forcep type comprising the combination of:
   an instrument body having a downwardly extendig handle portion;
   a handle lever pivotally carried on said instrument body;
   an elongated tube having one end secured to said instrument body outwardly projecting normal to said handle portion to terminate in a free end;
   a jaw arrangement operably to open and close in response to movement of said handle lever;
   a gear arrangement movably carried on said tube and coupled to asid jaw arrangement; and
   an actuation rod movable within said tube having one end secured to said gear arrangement and its other end pivotally secured to said handle lever.

2. The invention as defined in claim 1 including:
   a travel limit stop means operably interconnecting said handle portion with said handle lever for retaining said jaw arrangement in a fixed position.

3. The invention as defined in claim 1 including:
   an electrode carried on said instrument body;
   a conductive pellet interconnecting said electrode with said tube; and
   insulative material surrounding said tubing and said electrode to electrically insulate said instrument body and said tubing exterior from said electrode while providiing electrical communication with said gear arrangement.

4. The invention as defined in claim 1 wherein:
   said gear arrangement comprises a spherical piston gear reciprocally operating within a gear chamber carried on said tubing free end.

5. The invention as defined in claim 4 wherein:
   said piston gear includes a body having an open-ended bore with internal gear teeth;
   said jaw arrangement includes external gear teeth disposed through said open-ended bore in mesh with said internal gear teeth.

6. The invention as defined in claim 1 wherein:
   said gear arrangement includes an elongated bar having aligned openings;
   said jaw arrangement having gear teeth in mesh with said bar openings.

7. The invention as defined in claim 1 wherein:
   said gear arrangement includes a cylindrical member having a pair of spaced elements;
   each element having gear teeth facing teeth on the opposing element; and
   said jaw arrangement having gear teeth in mesh with said element gear teeth.

* * * * *